United States Patent [19]

Zardi et al.

[11] 4,082,797
[45] Apr. 4, 1978

[54] METHOD FOR THE CONDENSATION OF CARBAMMATE IN UREA-SYNTHESIS INSTALLATIONS

[75] Inventors: Umberto Zardi, San Donato Milanese (Milan); Vincenzo Lagana', Milan; Andrea Bonetti, San Donato Milanese (Milan); Giorgio Schmid, Lodi, all of Italy

[73] Assignee: Snamprogetti, S.p.A., Milan, Italy

[21] Appl. No.: 678,635

[22] Filed: Apr. 20, 1976

[30] Foreign Application Priority Data

Apr. 23, 1975 Italy ................................ 22615 A/75

[51] Int. Cl.$^2$ .................... C07C 126/00; C07C 126/02
[52] U.S. Cl. ................................................ 260/555 A
[58] Field of Search ................... 260/555 A; 165/110; 122/34

[56] References Cited

U.S. PATENT DOCUMENTS

| 2,302,993 | 11/1942 | Graham | 122/34 |
| 2,560,070 | 7/1951 | Bloomer | 122/34 |
| 3,607,938 | 9/1971 | Braun | 260/555 A |
| 3,940,440 | 2/1976 | Mavrovic | 260/555 A |
| 3,984,469 | 10/1976 | Guadalupi et al. | 260/555 A |

OTHER PUBLICATIONS

"Hydrocarbon Processing", Nov. 1971, p. 216.
"Applied Process Design for Chemical and Petrochemical Plants", vol. 3, Chapter 10, 1965, pp. 1-8.

*Primary Examiner*—Edward J. Meros
*Attorney, Agent, or Firm*—Thomas M. Hammond

[57] ABSTRACT

In a urea-synthesis installation, the problem of the condensation of the ammonium carbamate is solved by providing a condensation zone composed of a horizontal tube bundle which is placed under the static pressure of a liquid head. The ratio of the liquid head height to the diameter of the circumference encompassing the outermost tube layer of the bundle of tubes is critical: it should be between 5 and 30, 10 being the preferred value.

6 Claims, 2 Drawing Figures

METHOD FOR THE CONDENSATION OF CARBAMMATE IN UREA-SYNTHESIS INSTALLATIONS

This invention relates to a method for the condensation of carbamate in urea-synthesis installations.

In the various methods for the production of urea, exchangers are usually provided for condensing the vapours of $NH_3 + CO_2 + H_2O$ produced in the several stages of decomposition and recycling of the carbamate to the urea reactor.

The several procedures provide different systems for recycling the carbamate to the reactor in one or more operating stages at different pressures and temperatures.

In the stripping procedures almost all the carbamate is recycled in a single operating stage at a pressure which is substantially equal to that of the reactor and the vapours of $NH_3 + CO_2 + H_2O$ as obtained in the distiller (stripper) which also is operated at a pressure substantially equal to that of the reactor, are condensed in the carbamate condenser at a high temperature.

The heat evolved in said condensation is removed at a high heat level for the production of steam.

In the conventional processes the carbamate is recycled in a number of stages which operate at decreasing pressures, these being substantially different from those of the synthesis reactor. Only a fraction of the heat of condensation of the carbamate is recovered at a level which is high enough to produce steam in the carbamate condenser, the latter being operated at a higher pressure.

In all cases the condensation of vapours of $NH_3 + CO_2 + H_2O$ is a critical operation, especially in the fields of composition of the mixture $NH_3 + CO_2 + H_2O$ with low contents of $H_2O$ such as these which are encountered in the stages of carbamate recycling which operate at a higher pressure.

To make this condensation possible, especially when the vapours of $NH_3 + CO_2 + H_2O$ to be condensed come from a high-pressure distillation stage (and thus are poor in $H_2O$), the carbamate condenser is fed, along with the vapours, also with a carbonate solution which is rich in $H_2O$ as normally produced in the stages of condensation and recycle of the carbamate which are operated at a lower pressure. High pressure = 100 to 300 atmospheres; low pressure = 2 – 50 atmospheres. Said solution is an absorbent means and it is very important that a uniform distribution be achieved between the vapours of $NH_3 + CO_2 + H_2O$ and the added solution.

This result is obtained with the conventional techniques with appropriate systems for the mixing and distribution of the vapours and the solution of carbonate which has been added.

Figure 1:
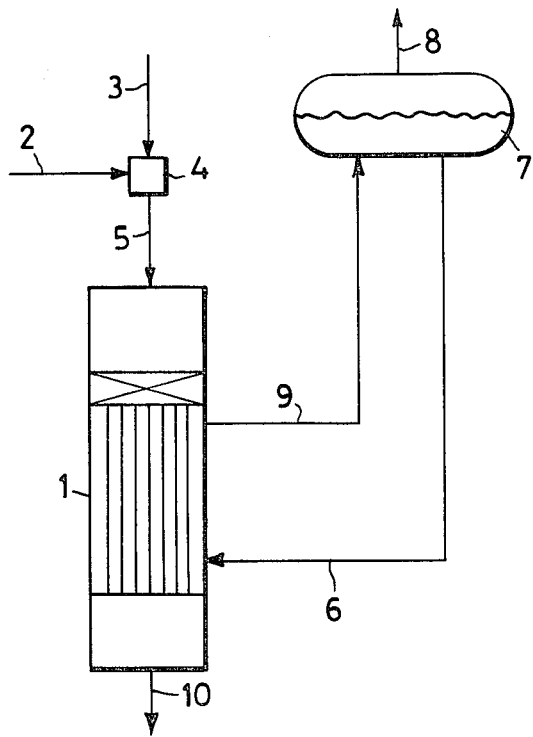
FIG. 1 is a schematic representation of a prior art carbamate condensation system wherein the carbamate condenser is a vertical tubes heat exchanger.

In the past, in order to achieve an even distribution of the vapours plus the absorbent liquor, the carbamate condensers which are operated at the higher pressures, are generally made of the vertical type with the processing fluids in the interior of the tubes. The condensation is carried out according to the diagram of FIG. 1 of the accompanying drawing. The vapours of $NH_3 + CO_2 + H_2O$ are fed through the line 3 and, in the mixer 4, are admixed with the ammonium carbonate solution coming from the low-pressure stages and fed in through the line 2. The mixture, through the line 5, feeds the vertical condenser 1 in the jacket of which water, fed in through 6, is circulated. The water vapours which are produced emerge from the jacket of the condenser 1 through the line 9 and go to the steam separator 7 from which water 6, and the as-produced steam 8, are drawn.

The solution of ammonium carbamate which is produced is discharged through 10.

When heat is removed by the production of steam as has been seen, there is also provided an apparatus for separating the as-produced steam, which is properly connected to the carbamate condenser.

Inasmuch as an even distribution of the liquid and the vapours is extremely critical to the ends of a correct operation of the condenser, and in order to obtain the heat evolved in the condensation of the $NH_3 + CO_2 + H_2O$ vapours at the highest possible level, expensive distribution systems are usually provided at the exchanger inlet.

It is a cumbersome task to insure a correct operation of said distributors and to bar preferential paths since clogging phenomena are likely to occur, as a result of the crystallization of the carbamate.

In addition, it is extremely expensive to provide a vertical exchanger on account of the supporting structures it requires, especially in installations having a high potential output and when also a separator is provided for the steam which is produced with the removal of heat. It is very difficult, moreover, to achieve an even distribution when the apparatus has a considerable bulk (high-output installations).

It has been surprisingly found, and this is the subject matter of this invention, that, if the mixture formed by the (compressed) solution of ammonium carbonate coming from the low-pressure stage and by the $NH_3$, $CO_2$ and $H_2O$ vapours coming from the decomposition of the carbamate at a high pressure (the pressure of such a mixture ranges from 50 to 300 atmospheres), is introduced in a horizontal tubular condensation zone at an inlet pressure of from 50 to 300 atmospheres maintained under a static "head" $\Delta P$, all the above enumerated drawbacks are easily overcome.

The value of $\Delta P$ ranges from 0.5 to 5 atmospheres and can be obtained with any system known from the prior art, such as for example a reduction valve, but preferably is attained by a liquid "head" at the outlet ($\Delta H$).

The method according to the present invention can advantageously be carried out with a condenser having a bundle of horizontal tubes and a liquid heat at the outlet, in which the ratio of the liquid head $\Delta H$ to the diameter D, of the circumference which encompasses the outermost tubes of the bundle of horizontal tubes is preferably comprised between 5 and 30, and is preferably 10.

The solution having a liquid content over 20% enters the tubes and is condensed and the solution is discharged from the condenser whereas the heat of condensation is exploited to produce steam in the condenser jacket.

The invention is now described with reference to FIG. 2 which is by no means to be construed as a limitation.

The horizontal tube condenser 1 is fed with the carbonate solution (2) coming from the low-pressure decomposition stages and the gaseous mixture (3) formed by $CO_2 + NH_3 + H_2O$ coming from the high-pressure decomposition of the carbamate. The horizontal evaporation is equipped with a discharge tube 5 which makes it possible to keep the desired $\Delta H$, (6) which is overcome by the mixture of carbonate and the condensed vapours of $NH_3$, $CO_2$ and $H_2O$. The as-produced steam leaves the evaporator 1 through the tube 4.

The advantages of the method according to the invention are:

1. A reduction of invested capital (the distribution system is dispensed with, the supporting structures are reduced, steam separator is dispensed with in the case in which the heat is removed by producing steam)
2. Reliability of operation under optimum conditions without crystallization or preferential paths.
3. Removal of heat at the maximum level (production of better quality steam) when the condensation takes place at a high pressure.

An example will now be given, which aims at better illustrating the invention.

EXAMPLE

Figure 2:
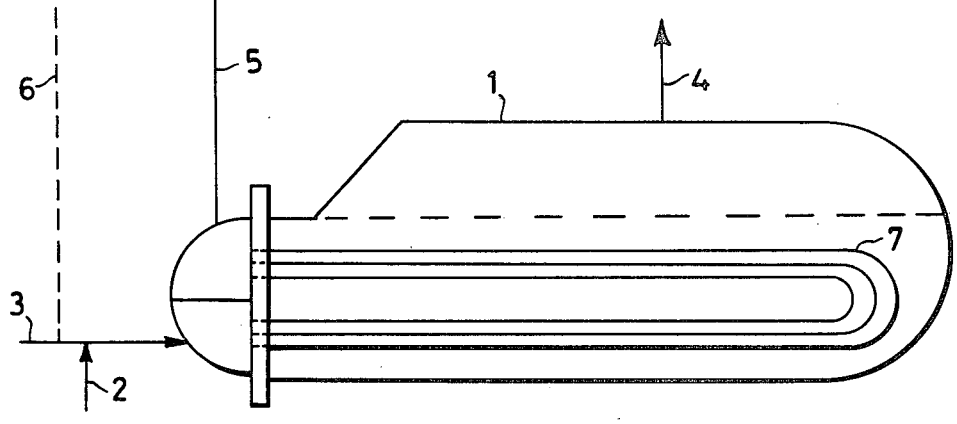
FIG. 2 is a schematic representation of a carbamate condensation system wherein the carbamate condenser is a horizontal-tube-bundle heat exchanger embodying our invention.

Let a Kettle type, horizontal-tube-bundle exchanger 1, be considered (see FIG. 2).

The vapours 3 at the pressure of 150 atmospheres (temperature = 190° C, rate of flow = 60 tons) coming from the carbamate decomposition section (not shown) and composed of $NH_3 + CO_2 + H_2O$, are condensed in the interior of the tubes 7, of the tube-bundle after having been admixed with an aqueous solution 2, of ammonium carbonate, recycled from the low-pressure section and previously pumped at 150 atmospheres (temperature of the solution 70° C; rate of flow : 25 tons).

The heat is removed by boiling a liquid phase on the side of the jacket, the result being the production of steam 4.

A $\Delta H/D$ ratio equal to 10 is maintained and under these conditions the tubes of the horizontal tube condenser are completely filled with liquid and the condensation takes place unhindered.

The as-produced steam has a temperature of 147° C while a conventional apparatus is incapable of producing steam at a temperature higher than 138° C.

What we claim is:

1. A process for synthesizing urea which includes producing vapors of $NH_2 + CO_2 + H_2O$ through a high pressure distillation stage and feeding a mixture of said vapors and a carbonate solution which is rich in $H_2O$ to a carbonate condenser provided with a jacket through which water is circulated for the recovery of the heat of condensation by the production of steam and having a condensation zone where said vapors are condensed to produce a carbamate solution for recycle to a urea reactor, wherein the improvement comprises forming said condensation zone of a horizontal-tube-bundle and maintaining said condensation zone under a static head ($\Delta P$) in the range between 0.5 and 5 atmospheres.

2. A process for synthesizing urea as claimed in claim 1, wherein said horizontal-tube-bundle condensation zone has an outlet, including the step of maintaining a liquid head ($\Delta H$) at said outlet which is overcome by the mixture of said condensed vapors and carbonate solution.

3. A process for synthesizing urea as claimed in claim 2, wherein the ratio of the liquid head ($\Delta H$) to the diameter (D) of the circumference which encompasses the outermost tubes of said horizontal-tube-bundle is between 5 and 30.

4. A process for synthesizing urea as claimed in claim 3, wherein said ratio of the liquid head ($\Delta H$) to the diameter (D) of the circumference which encompasses the outermost tubes of said horizontal-tube-bundle is 10.

5. A process for synthesizing urea as claimed in claim 1, wherein said mixture which is fed to said carbamate condenser has a liquid content greater than 20%.

6. A process for synthesizing urea as claimed in claim 1, wherein said condensation and production of steam are concurrent.

* * * * *